US009168072B2

(12) United States Patent
Singhatat et al.

(10) Patent No.: US 9,168,072 B2
(45) Date of Patent: Oct. 27, 2015

(54) INFLATABLE INTERSPINOUS SPACER

(75) Inventors: Wamis Singhatat, Malvern, PA (US);
David Chow, West Chester, PA (US);
Nigel G. Smith, Norwich (GB);
Garland W. Fussell, Thorndale, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 333 days.

(21) Appl. No.: 12/995,480

(22) PCT Filed: Jun. 2, 2009

(86) PCT No.: PCT/US2009/045964
§ 371 (c)(1),
(2), (4) Date: Dec. 1, 2010

(87) PCT Pub. No.: WO2009/149079
PCT Pub. Date: Dec. 10, 2009

(65) Prior Publication Data
US 2011/0082504 A1     Apr. 7, 2011

Related U.S. Application Data

(60) Provisional application No. 61/057,985, filed on Jun. 2, 2008.

(51) Int. Cl.
*A61B 17/70* (2006.01)
*A61B 17/00* (2006.01)
(52) U.S. Cl.
CPC ... *A61B 17/7065* (2013.01); *A61B 2017/00557* (2013.01)
(58) Field of Classification Search
CPC ... A61B 17/7065–17/7068; A61B 2017/00557

USPC .................................................. 606/246–249
See application file for complete search history.

(56) References Cited

U.S. PATENT DOCUMENTS 4,824,436 A * 4/1989 Wolinsky ...................... 604/509
5,328,471 A * 7/1994 Slepian .................... 604/101.03
(Continued)

FOREIGN PATENT DOCUMENTS

WO     2007127677 A1    11/2007

OTHER PUBLICATIONS dictionary.com—http://dictionary.reference.com/browse/around?s=t—around. Retrieved on Nov. 27, 2012.*
(Continued)

*Primary Examiner* — Eduardo C Robert
*Assistant Examiner* — Jacqueline Johanas
(74) *Attorney, Agent, or Firm* — Meunier Carlin & Curfman LLC (57) ABSTRACT

The present invention is directed to an inflated interspinous spacer. The interspinous spacer is inserted into the interspinous space between adjacent spinous process in a deflated or unexpanded state, and is inflated or expanded with an injectable filler material. Upon inflation, the spacer preferably distracts the spinous processes and assumes a shape that retains the spacer in position and preferably mechanically locks with the spinous processes. The spacer includes two separate balloons configured to have different compressive modulus so that one balloon is softer and more deformable than the other balloon.

15 Claims, 3 Drawing Sheets

(56) References Cited

U.S. PATENT DOCUMENTS

| | | | |
|---|---|---|---|
| 5,549,679 A * | 8/1996 | Kuslich | 623/17.12 |
| 6,287,320 B1 * | 9/2001 | Slepian | 606/194 |
| 6,733,531 B1 * | 5/2004 | Trieu | 623/17.11 |
| 6,958,077 B2 * | 10/2005 | Suddaby | 623/17.11 |
| 8,038,698 B2 * | 10/2011 | Edidin et al. | 606/246 |
| 8,048,119 B2 * | 11/2011 | Bruneau et al. | 606/249 |
| 8,052,728 B2 * | 11/2011 | Hestad | 606/279 |
| 8,147,517 B2 * | 4/2012 | Trieu et al. | 606/248 |
| 8,147,526 B2 * | 4/2012 | Auyoung | 606/279 |
| 8,157,841 B2 * | 4/2012 | Malandain et al. | 606/249 |
| 8,221,465 B2 * | 7/2012 | Trieu et al. | 606/249 |
| 8,317,831 B2 * | 11/2012 | Auyoung et al. | 606/249 |
| 8,454,693 B2 * | 6/2013 | Malandain et al. | 623/17.11 |
| 2005/0251140 A1 * | 11/2005 | Shaolian et al. | 606/61 |
| 2005/0288678 A1 * | 12/2005 | Reiley et al. | 606/93 |
| 2006/0084983 A1 * | 4/2006 | Kim | 606/61 |
| 2006/0084988 A1 * | 4/2006 | Kim | 606/61 |
| 2006/0085069 A1 * | 4/2006 | Kim | 623/17.11 |
| 2006/0106397 A1 * | 5/2006 | Lins | 606/90 |
| 2006/0122620 A1 * | 6/2006 | Kim | 606/90 |
| 2006/0235387 A1 * | 10/2006 | Peterman | 606/61 |
| 2006/0235460 A1 * | 10/2006 | Reiley et al. | 606/192 |
| 2006/0247623 A1 * | 11/2006 | Anderson et al. | 606/61 |
| 2006/0293662 A1 * | 12/2006 | Boyer et al. | 606/61 |
| 2007/0043363 A1 * | 2/2007 | Malandain et al. | 606/61 |
| 2007/0073292 A1 * | 3/2007 | Kohm et al. | 606/61 |
| 2007/0191838 A1 * | 8/2007 | Bruneau et al. | 606/61 |
| 2007/0213760 A1 * | 9/2007 | Hayes et al. | 606/192 |
| 2007/0213829 A1 * | 9/2007 | Le Couedic et al. | 623/17.16 |
| 2007/0233074 A1 * | 10/2007 | Anderson et al. | 606/61 |
| 2007/0233076 A1 * | 10/2007 | Trieu | 606/61 |
| 2007/0250169 A1 * | 10/2007 | Lang | 623/17.12 |
| 2007/0270823 A1 * | 11/2007 | Trieu et al. | 606/61 |
| 2007/0270829 A1 * | 11/2007 | Carls et al. | 606/61 |
| 2007/0272259 A1 * | 11/2007 | Allard et al. | 128/898 |
| 2007/0276368 A1 | 11/2007 | Trieu et al. | |
| 2007/0276496 A1 * | 11/2007 | Lange et al. | 623/17.12 |
| 2007/0276497 A1 * | 11/2007 | Anderson | 623/17.12 |
| 2008/0058934 A1 * | 3/2008 | Malandain et al. | 623/17.11 |
| 2008/0114357 A1 * | 5/2008 | Allard et al. | 606/61 |
| 2008/0167685 A1 * | 7/2008 | Allard et al. | 606/246 |
| 2008/0172081 A1 * | 7/2008 | Reiss et al. | 606/192 |
| 2008/0281426 A1 * | 11/2008 | Fitz et al. | 623/17.16 |
| 2009/0024166 A1 * | 1/2009 | Carl et al. | 606/247 |
| 2009/0036926 A1 * | 2/2009 | Hestad | 606/247 |
| 2009/0118833 A1 * | 5/2009 | Hudgins et al. | 623/17.16 |
| 2009/0216274 A1 * | 8/2009 | Morancy-Meister et al. | 606/247 |
| 2009/0299373 A1 * | 12/2009 | Sisken | 606/92 |
| 2010/0042151 A1 * | 2/2010 | Anderson | 606/249 |
| 2011/0172710 A1 * | 7/2011 | Thommen et al. | 606/249 |
| 2011/0190817 A1 * | 8/2011 | Thommen et al. | 606/249 |

OTHER PUBLICATIONS

International Search Report, dated Oct. 21, 2009, received from the European Patent Office in connection with International Application No. PCT/US2009/045964.

International Preliminary Report on Patentability and Written Opinion, dated Dec. 6, 2010, received from the European Patent Office in connection with International Application No. PCT/US2009/045964.

* cited by examiner

INFLATABLE INTERSPINOUS SPACER

CROSS REFERENCE TO RELATED APPLICATIONS

This application is the National Stage of International Application No. PCT/US09/45964, filed Jun. 2, 2009, which claims the benefit of priority to U.S. Provisional Patent Application No. 61/057,985, filed Jun. 2, 2008, the disclosures of which are hereby incorporated by reference in their entireties.

FIELD OF THE INVENTION

The present invention relates generally to orthopedics. More specifically, the present invention relates to an inflatable interspinous spacer preferably insertable via a minimally invasive surgical procedure.

BACKGROUND OF THE INVENTION

Interspinous spacers are indicated for the treatment of spinal stenosis and treatment of low back pain caused by, for example, disc- or facet-related degeneration. Interspinous spacers may be configured to distract and/or maintain the spacing between adjacent superior and inferior spinous processes above and below the painful disc level.

Most interspinous spacers in clinical use are made of a hard, undeformable material under normal physiological loads, such as metal or PEEK. There is an increasing concern, supported by recent clinical study data, that suggests hard spacers may subside into the bony spinous processes over time, thus losing their therapeutic effect. Softer spacers could potentially avoid subsidence by distributing loads over a larger area of the spinous processes. Moreover, soft spacers may be gentler to the portions of the bony spinous processes between which they interface.

Further, inflatable interspinous spacers may be desirable in that they may be well-suited for a truly percutaneous solution that may enable tissue damage, the size of the surgical incision and the resultant risk of infection and recovery time to be minimized.

BRIEF SUMMARY OF THE INVENTION

In one embodiment, the present invention is directed to an inflatable interspinous spacer. The spacer is inserted into the interspinous space in a deflated or unexpanded state, and is inflated or expanded with an injectable filler material. Upon inflation, the spacer preferably distracts the spinous processes and assumes a shape that preferably retains the spacer in position and preferably mechanically locks with the spinous processes. The spacer preferably includes two separate balloons configured to have different compressive modulus so that one balloon is softer and more deformable than the other balloon.

In one exemplary embodiment, the inflatable interspinous spacer for insertion into an interspinous space between adjacent superior and inferior spinous processes via a minimally invasive surgical procedure includes a first balloon, a first filler material, a second balloon and a second filler material. The first balloon may have a first end portion, a second end portion and a central portion located between the first and second end portions. The first end portion, the second end portion and the central portion are preferably in fluid communication with each other. The first balloon is preferably manufactured from a low compliant material so that upon inflation, the first balloon assumes a predetermined shape. In use, the first balloon is inflated from an insertable deflated condition to an inflated expanded condition. The first filler material is configured for introduction into the first balloon to cause expansion of the first balloon and in particular, expansion of the first end portion, the second end portion and the central portion.

The second balloon is preferably in the form of a hollow cylinder and is preferably disposed about at least a portion of the central portion of the first balloon. In use, the second balloon is inflated from an insertable deflated condition to an inflated expanded condition. The second filler material is configured for introduction into the second balloon to cause expansion of the second balloon.

In the insertable deflated condition, the spacer is preferably laterally insertable into the interspinous space between adjacent spinal processes without substantially altering the spinal processes such that at least a portion of the central portion of the first balloon and at least a portion of the second balloon is located in the interspinous space between the adjacent spinous processes. In the inflated expanded condition, the height of the first and second end portions of the first balloon are larger than the height of the central portion of the first balloon. That is, the first and second end portions of the first balloon have first and second heights, respectively, and the central portion of the first balloon has a third height, the first and second heights of the first and second end portions are larger than the third height of the central portion when in the inflated expanded condition. Accordingly, the spacer in the inflated expanded condition may form an "H" or dumbbell-like shape or form. In addition, in the inflated expanded condition, the first and second end portions of the first balloon are preferably located along the lateral sides of the adjacent spinous processes to retain the spacer in position between the spinous processes, the second balloon is disposed over the central portion of the first balloon, and the second balloon is preferably less rigid than the first balloon. The second balloon and the central portion of the first balloon in the inflated expanded condition and when located between the spinous processes may limit extension of the spine. The compressive modulus of the second filler material may be less than the compressive modulus of the first filler material.

The expansion of the second balloon may distract and expand the interspinous space between the adjacent spinous processes where the spacer is located. The second balloon may form a hollow substantially cylindrical shape disposed about the central portion of the first balloon and may form a common wall or surface with at least a portion of the central portion of the first balloon. The second balloon may also be disposed over at least a portion of the first end portion and the second end portion. The second balloon may be manufactured from a low-compliant material so that upon inflation, the second balloon assumes a predetermined shape. Alternatively however the second balloon is preferably manufactured with a non-predetermined shape upon inflation. For example, the second balloon is preferably manufactured from a semi-compliant or highly compliant material so that the second balloon may elastically or plastically stretch so as to conform to the shape of the spinous processes to increase the surface area contact between the spacer and the inferior and superior surfaces of the adjacent spinous processes. The second balloon may absorb compressive shocks to the spacer. The spacer without the first or second filler materials contained within the first and second balloons may be insertable within a cannula having a 5 mm inside diameter.

In another embodiment, the inflatable interspinous spacer for insertion between spinous processes includes first and second balloons, the inflated interspinous spacer forming a central zone, a first end zone and a second end zone. The two-balloon spacer having an insertable deflated condition and an inflated expanded condition wherein in the insertable deflated condition, the spacer is insertable within a cannula having a 5 mm inside diameter, and in the inflated expanded condition a portion of each of the first and second end zones is larger than the central zone, the central zone being positionable in the interspinous space between adjacent spinous processes to limit extension of the spine.

The second balloon preferably surrounds at least a portion of the first balloon, and more preferably, at least a portion of the central zone. The second balloon is preferably configured, in the inflated expanded condition, to contact at least a portion of the adjacent spinous processes. The second balloon, in the inflated expanded condition, being less rigid than the first balloon and being configured to conform to the shape of the contacted spinous process in order to increase the area of contact between the spinous process and the second balloon.

In another embodiment, the inflatable interspinous spacer for insertion between adjacent spinous processes via a minimally invasive surgical procedure of the spine preferably includes a first inflatable member, a first filler material, a second inflatable member and a second filler material. The first inflatable member having an inflated and a non-inflated state, and may include a first end portion, a central portion, and a second end portion, wherein the height of the first and second end portions is larger than the height of the central portion in the inflated state. As such, the first inflatable member preferably assumes an "H" or dumbbell-like shape.

The first filler material is preferably configured for introduction into the first inflatable member to thereby cause expansion of the first inflatable member. The second inflatable member may be characterized by a hollow cylindrical form, wherein the second inflatable member is disposed around at least a portion of the central portion of the first inflatable member. The second filler material is preferably configured for introduction into the second inflatable member to thereby cause the expansion of the second inflatable member. The modulus of the first filler material may be larger than the modulus of the second filler material.

In still another embodiment, the rigidity of the second inflatable member, upon expansion of the first and second inflatable members, is less than the rigidity of the first inflatable member.

BRIEF DESCRIPTION OF THE SEVERAL VIEWS OF THE DRAWINGS

The foregoing summary, as well as the following detailed description of the preferred embodiments of the application, will be better understood when read in conjunction with the appended drawings. For the purposes of illustrating the inflatable interspinous spacer of the present application, there is shown in the drawings preferred embodiments. It should be understood, however, that the application is not limited to the precise arrangements, structure, features, embodiments, aspects and instrumentalities shown and that the features, structures and aspects shown may be used singularly or in combination with other features, structures and aspects. In the drawings.

DETAILED DESCRIPTION OF THE INVENTION

Certain terminology is used in the following description for convenience only and is not limiting. The words "right", "left", "lower", "upper", "top" and "bottom" designate directions in the drawings to which reference is made. The words "inwardly" and "outwardly" refer to directions toward and away from, respectively, the geometric center of the spacer, and designated parts thereof. The words, "anterior", "posterior", "superior", "inferior", "lateral", "medial" and related words and/or phrases designate preferred positions and orientations in the human body to which reference is made and are not meant to be limiting. The terminology includes the above-listed words, derivatives thereof and words of similar import.

Figure 1:
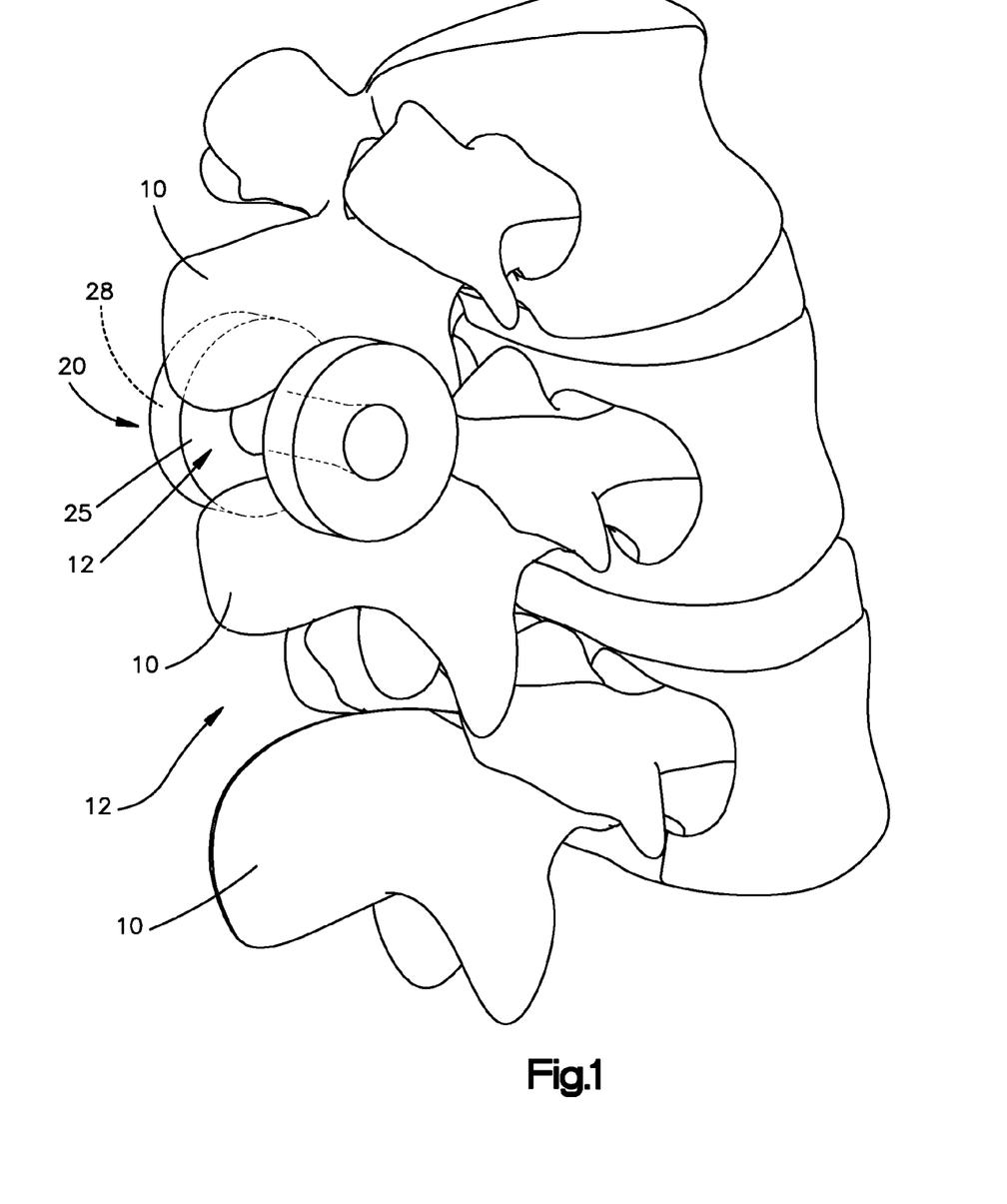
FIG. 1 illustrates an inflatable interspinous spacer inserted between adjacent spinous processes.

FIG. 1 illustrates an inflatable interspinous spacer 20 that includes a housing 25 and an injectable filler material 28. The spacer 20 is preferably inserted into the interspinous space 12 in a deflated nonexpanded state, and is inflated or otherwise expanded with the injectable filler material 28. Upon expansion, the spacer 20 preferably distracts the spinous processes 10 and assumes a shape that is retained between, and preferably mechanically locks with the spinous processes 10.

Figure 2:
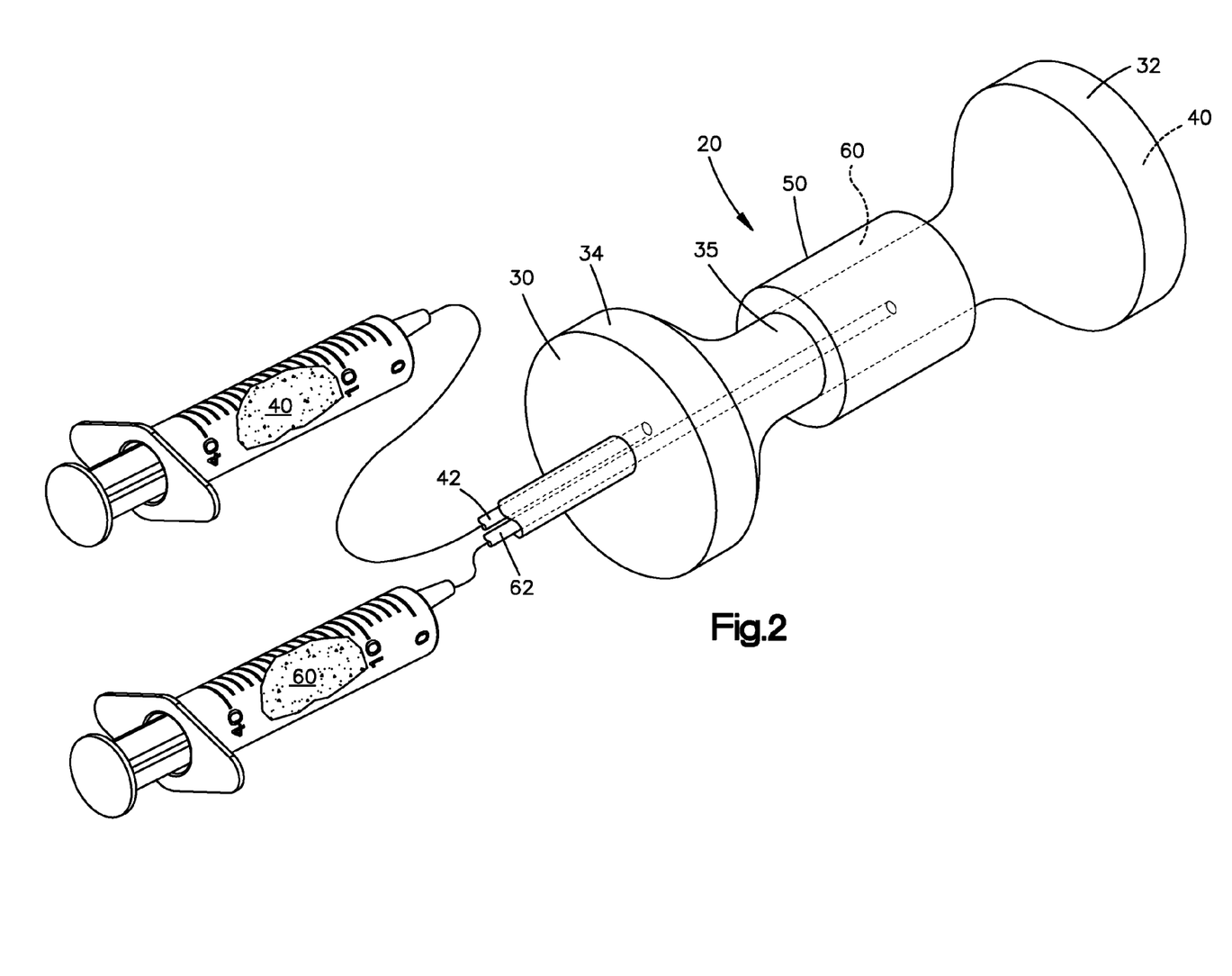
FIG. 2 illustrates a perspective view of a preferred embodiment of an inflatable interspinous spacer in accordance with the present invention.

In a preferred embodiment, shown in FIG. 2, the spacer 20 includes a first balloon or inflatable cavity 30 and a second balloon or inflatable cavity 50. The first balloon 30 preferably is manufactured from a low-compliant material so that the first balloon 30 takes on a predetermined shape, such as, for example, a "dumb-bell" shape, upon expansion with a first filler material 40, due to the material and manufactured shape of the first balloon 30. The second balloon 50, preferably surrounds at least a portion of the first balloon 30, and more preferably the region located within the interspinous space 12 between the adjacent spinous process 10 of the first balloon 30. The second balloon 50 upon inflation with a second filler material 60, expands radially preferably to distract the spinous processes 10. The second balloon 50 is preferably a hollow cylindrical sleeve although other shapes are contemplated. The amount of distraction may be adjusted by controlling the volume and/or pressure of inflation of the second balloon 50 with the second filler material 60. The shape and configuration of the spacer 20 preferably retains the spacer 20 between the spinous processes 10 and preferably provides a mechanical lock with the spinous processes 10 for improved spacer 20 stability. While the spacer 20, and in particular, the first balloon 30 are shown as "dumb-bell" shaped, other shapes for the spacer 20 and/or the first balloon 30 are contemplated, such as, for example, an "H-shape", or preferably other shapes that may have enlarged end portions to assist in retaining the spacer 20 in position in the body.

In use, the inflatable interspinous spacer 20 is inserted into the interspinous space 12 between adjacent spinous processes 10. The interspinous spacer 20 preferably includes two balloons 30, 50 and preferably is inserted laterally in the space 12 between adjacent spinous processes 10. The spacer 20 is inserted between the spinous process 10 in a deflated nonexpanded condition or state that preferably fits through the space 12 between spinous processes 10 by a lateral insertion technique with little to no modification of the interspinous space 12 or spinal processes 10. As such, the spacer 20 and, in particular, the first and second balloons 30, 50 are preferably flexible and collapsible into a small, deflated insertion configuration or shape so that the spacer 20 can be inserted through a small opening, incision or cannula.

The first balloon 30 may be any biocompatible material now or hereafter known for such purpose. The first balloon 30 is preferably formed of a flexible, low-compliant material. The material for the first balloon 30 is preferably low compliant so that it will hold its shape without substantially stretching and is preferably flexible so that it can be folded and packaged into a small size and shape for insertion into the inter-spinal space 12. For example, the first balloon 30 may be manufactured from a non-compliant material such as, polyetherketoneketone (PEKK), polyethyleneterephthalate (PET), etc. More preferably, the first balloon may be manufactured from polyetheretherketone (Optima PEEK).

Alternatively, the first balloon 30 may be manufactured from a semi or highly-compliant material. For example, the first balloon 30 may be manufactured from a semi-compliant material such as polycarbonateurethane (PCU), Bionate 75D, Bionate 55D, PEBAX, nylon, low density polyolefins including, for example, polyethylene, polypropylene, etc. Moreover, the first balloon 30 may be manufactured from a highly compliant material such as polycarbonate urethanes including, for example, Bionates, Carbosil, etc., polyether urethane silicone including, for example, modified Elasteon, polyester urethanes including, for example, Estanes, silicone elastomers, latex natural rubber (vulcanized), nitrile latex rubbers (vulcanized), etc.

When using a semi or highly-compliant material, the first balloon 30 may be rigidly constrained along its central zone 35 via, for example, a cylindrical member such as, for example, a catheter, such that upon expansion by the first filler material 40, the first balloon 30 achieves a "dumb-bell" shape without having a predetermined balloon shape.

Moreover, as will be appreciated by one of ordinary skill in the art, the spacer 20 may alternatively be inserted via a posterior or posterolateral mini-open approach to the adjacent spinous processes, whereby the surgeon gains access to the implantation site via surgical dissection and exposes the lateral aspect of the interspinous ligament to permit lateral delivery of the spacer.

As previously mentioned, the first balloon 30 preferably expands to a predetermined size and shape upon being filled with the first filler material 40 via, for example, because it is manufactured from a low-compliant material or because it is constrained. Preferably, the first balloon 30 has a central region or zone 35 located between two end regions or zones 32, 34. In use, the central zone 35 is preferably positioned in the interspinous space 12 between the adjacent spinous processes 10. The end zones 32, 34 are lateral of the central zone 35 and preferably, in the inflated expanded configuration, are enlarged so that at least a portion of the end zones 32, 34 is larger than the central zone 35 and/or interspinous space 12, so that at least a portion of the end zones 32, 34 are adjacent the sides of the adjacent spinous processes 10. The end zones 32, 34 may be the same or different shapes and may be generally disc shaped as shown or any one of a number of other shapes. The end zones 32, 34 preferably retain the spacer 20 between the spinous processes 10 to prevent the lateral expulsion, migration or movement of the spacer 20. The central zone 35 may be cylindrically shaped as shown, or any other shape, such as, for example, shapes having a cross section that is oval, square, rectangular, hexagonal, etc. The first balloon 30 is preferably expanded by inserting the first filler material 40 through a filling tube 42 as shown in FIG. 2.

The spacer 20, and in particular the first and second end zones 32, 34 of the first balloon 30 may be configured so that, upon inflation, the end zones 32, 34 contact and/or hold the sides of the adjacent spinous processes 10. The spacer 20, and in particular the first and second end zones 32, 34 of the first balloon 30 may expand to squeeze and press against the spinous process 10 to mechanically interlock with the spinous process 10.

While the first and second end zones 32, 34 and the central zone 35 are shown as one continuous compartment, each zone 32, 34, 35 may be an independent compartment with separate filling tubes, or two or more of the zones 32, 34, 35 may be combined and use a single filling tube. While the spacer 20 has been described as having three zones, the first balloon 30 may have one or more zones and is not limited to the shape or number of zones shown and described.

The first filler material 40 is preferably injected in a flowable state and takes on a semi-rigid hardness or green strength upon curing in its implanted state. When the first filler material 40 is injected into the first balloon 30, the resulting construct provides structural form and stability to the interspinous spacer 20. The first filler material 40 may be any biocompatible material now or hereafter known for such purpose including, but not limited to, saline, air, gas, water, any of the family of injectable in-situ curing polymers now or hereafter used in the body, such as, for example, polyurethanes, silicones, or hydrogels. Preferably however the first filler material 40 is a thermogelling transforming polymer, a phase transforming polymer or a thermo-setting polymer with a variety of moduli. The utilization of a such polymers to expand the first balloon 30 enables the surgeon to optimize the first balloon 30 for his/her particular application by varying the properties of the spacer 20 and/or the cured polymer to possess structural properties similar to the natural vertebrae. U.S. patent application Ser. No. 10/837,082 to Lowman et al., filed on Nov. 4, 2004 and entitled "Thermogelling Polymer Blends for Biomaterial Applications", which is hereby incorporated by reference in its entirety, discloses a thermogelling material in the form of a PniPaam copolymer that transitions slightly below body temperature into an elastic solid. By forming into an elastic solid within the spacer, disadvantages associated with leaking of a liquid filled container may be overcome.

Referring to FIG. 2, the second balloon 50 preferably surrounds the central zone 35 of the first balloon 30. The first and second balloons 30, 50 may share a common wall or surface. The second balloon 50 may further include one or more protrusions, barbs, ridges, or other mating features to securely engage receiving features on the first balloon 30. The second balloon 50 preferably is flexible and collapsible into a smaller size and insertion shape so that the second balloon 50 can be inserted through a small incision, opening or cannula. Preferably the second balloon 50 is inserted in combination and/or in conjunction with the first balloon 30 as a unitary spacer. Preferably the second balloon 50 is flexible and collapsible so that the spacer 20 can be inserted laterally between the spinous processes 10 with little to no modification of the interspinous space 12 or spinal processes 10. The second balloon 50 preferably expands to a second, inflated size and shape when filled by a second filler material 60. The size and shape of the second balloon 50 may be a cylindrical tube as shown in FIG. 2, or can form any other shape, such as for example, a shape having a cross-section that is oval, square, rectangular, hexagonal, etc. As shown, the second balloon 50 preferably includes a central longitudinal lumen to accommodate the first balloon 30. The second balloon 50 may be formed of a flexible, low compliant material (examples of which were previously described in connection with the first balloon 30) to form a predetermine shape upon expansion. In this manner, the second balloon 50 may expand to a predetermined diameter and/or height to control the amount of distraction (in which case, several spacer sizes can be offered). Alternatively however the second balloon 50 is preferably manufactured from a semi-compliant or compliant material (examples of which were previously described in connection with the first balloon 30), so that the second balloon 50 can expand to a variety of diameters and/or thicknesses (and thus provides various amounts of distraction) controlled by the amount of second filler material 60 injected. As shown in FIG. 2, the thickness or height of the second balloon 50 is less than the length of the second balloon 50 as measured along the central longitudinal lumen of the second balloon. Barium sulfate, or some other contrast agent, may be integrated into the filler materials 40, 60 to permit visualization of the first and/or second balloons 30, 50 under fluoroscopy.

The second balloon 50 may be filled with the second filler material 60 by a second filling tube 62. The second filling tube 62 may extend within and through a portion of first balloon 30 with an opening into the interior of the second balloon 50 as shown in FIG. 2. Alternatively, the second filling tube 62 may extend from the second balloon 50 without passing through the first balloon 30.

The second filler material 60 is preferably injected in a flowable state and cures to a lower compressive modulus than the first filler material 40. When the second filler material 60 is injected into the second balloon 50, the resulting construct may provide distraction (expansion force) to the adjacent spinal processes 10 while maintaining a "cushioning" effect on the spinous processes 10. Expansion of the second balloon 50 may be constrained in the axial direction by the expanded ends 32, 34 of the first balloon 30, providing for controlled expansion of the second balloon 50 to a precise amount of distraction. The second filler material 60 may be any biocompatible material now or hereafter known for such purpose including, but not limited to, those described above for the first filler material 40, only tailored in chemistry preferably to provide for a lower compressive modulus upon curing. Alternatively however the second filler material 60 may have the same or a higher compressive modulus than the first filler material 40 upon curing. For example, the second filler material 60 may be a bone cement such as PMMA.

Since the spacer 20 preferably includes two inflatable balloons 30, 50, the interspinous spacer 20 may be delivered in a non-inflated state down a relatively small operating cannula (e.g. 5 mm inner diameter), thus enabling a truly percutaneous method of implantation. The first balloon 30 is preferably expanded first, followed by the second balloon 50. The spacer 20 may include more than two inflatable balloons such as, for example, three, four or more balloons.

In use, the spacer 20 is inserted laterally between the spinous processes 10 into the interspinal space 12, preferably without modifying the spinal processes 10 or other parts of the vertebrae, and by removing none, a portion, or the entire interspinous ligament using known minimally-invasive tissue dissection tools (e.g. rongeurs) to accommodate and allow for adequate expansion of the spacer 20. Preferably, the spacer 20 is placed into the patient via a lateral insertion technique from the side of the patient. The first balloon 30 is then expanded by filling it with the first filler material 40 to provide stability to the spacer 20 and position the spacer 20. The second balloon 50 preferably is thereafter filled with the second filler material 60. Preferably as a result of the second balloon 50 being expanded and filled with a lower modulus filling material, the second balloon 50 will preferably conform about the spinous processes 10 to increase the surface area contact with the spinous process 10 and spread any force transferred to the spinous process 10 over a larger area. Meanwhile, the first balloon 30 with its filler material adds structural integrity and stability to the spacer 20. The softer second balloon 50 may also permit the spacer 20 to have a dampening or cushioning structure or feature to absorb the shocks of suddenly applied loads.

Figure 3:
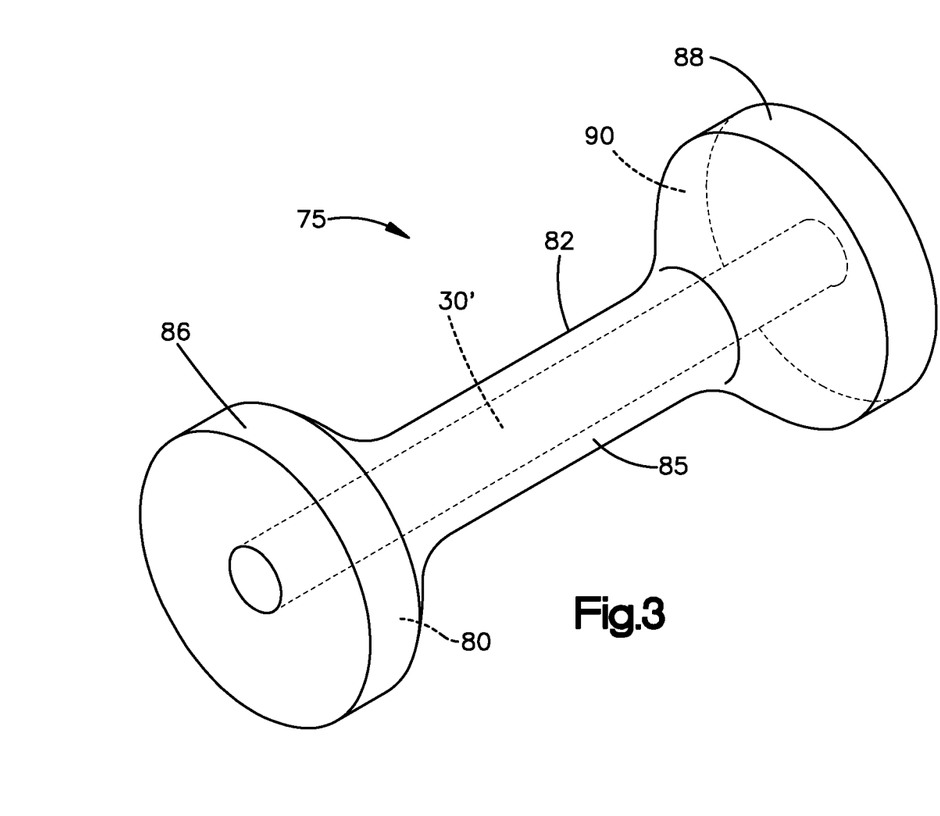
FIG. 3 illustrates a perspective view of an alternative embodiment of an inflatable interspinous spacer in accordance with the present invention.

Referring to FIG. 3, in an alternate embodiment, the first balloon and the first filler material may be replaced with a rigid component 30'. For example, the first rigid component 30' may comprise a rigid polyurethane, or other material such as PEEK, stainless steel, titanium or other biocompatible material. The first component 30' may be a rod or other support member that has rigidity and may have some flexibility. The first component 30' may include either fixed or deployable "stops" to engage the spinous processes 10, such that it takes on, for example, an "H" shape in its final configuration. Alternatively and/or in addition, the spacer 75 may include an inflatable balloon or housing 82 surrounding at least a portion of the first component 30'. The inflatable balloon or housing 82 forms an inner cavity or compartment 80 that preferably is inflatable with a filler material 90. The inflatable balloon or housing 82 preferably is formed of a flexible, low-compliant material. The inflatable balloon or housing 82 preferably is flexible and collapsible into a small insertion shape and size that preferably is about the size and shape of the first component 30' and preferably can be inserted through a small opening, incision or cannula (e.g., through about a 5 mm opening).

The inflatable balloon or housing 82 preferably includes a first end zone 86, a second end zone 88 and a central zone 85 located therebetween. The end zones 86, 88 are preferably positioned lateral of the central zone 85 and preferably are enlarged, in the inflated expanded configuration, so that at least a portion of the first and second end zones 86, 88 are larger than the central zone 85, and/or the interspinous space 12. The first and second end zones 86, 88 preferably retain the spacer 75 between the spinous processes 10 while the central zone 85 preferably contacts the superior and inferior surfaces of the adjacent spinous processes 10. The first and second end zones 86, 88 and the central zone 85 are preferably in fluid communication.

The inflatable balloon or housing 82 preferably expands from the deflated nonexpanded configuration to the inflated expanded configuration via injection of the filler material 90. The size and shape of the inflatable balloon or housing 82 may be "dumb-bell shaped" as shown, "H-shaped" or any other shape. The filler material 90 is preferably injected in a flowable state and preferably cures to a lower compressive modulus than the first component 30' so that the inflatable balloon or housing 82 is softer relative to the first component 30'. When the filler material 90 is injected into the inflatable balloon or housing 82, the resulting spacer 75 may distract the spinal processes 10 while maintaining a "cushioning effect" on the spinal processes 10. The balloon or housing 82 is preferably manufactured from a low-compliant material such that it inflates to a pre-determined diameter and/or height and/or shape to control the amount of distraction. Preferably, as a result of the balloon or housing 82 being formed of a relatively flexible material and filled with a preferred and predetermined relative low compressive modulus material, the balloon or housing 82 conforms about the spinous processes 10 to minimize point contact and thus increase the surface area contact between the spinous processes 10 and spread any force transferred to the spinous processes 10 over a larger area. The softer balloon or housing 82 may also permit the spacer 75 to have a dampening or cushioning effect to absorb shocks of suddenly applied loads. Alternatively however the filler material 90 may have the same or a higher compressive modulus than the first component 30' upon curing.

As previously mentioned, the first and second filler materials 40, 60 may be any biocompatible material now or hereafter known for such purpose. Preferably however the first and second filler materials 40, 60 may be a thermogelling transforming polymer, a phase transforming polymer or a thermo-setting polymer. Additional filler materials 40, 60 that may be used in conjunction with the spacer 20, 75 include for example, ultraviolet (UV) curable materials and other cross linking chemistries such as polymethylmethacrylate curing bone cements. UV curing materials are typically acrylates or methacrylates. In use, UV curing materials can be injected into the spacer and, when the first and/or second balloons are at the desired fill pressure or volume, a UV light source can be used to initiate the curing reaction to form the final polymer material. In addition, different monomeric materials can be used to tailor the mechanical properties of the filler material. Because the reaction can be initiated at the surface and propagate inward, the risk of leaching of unreacted components is generally limited. The UV light source can be used at the surface of the spacer (i.e. at an injection port or hole formed in the spacer), inserted into the interior of the spacer, or both. Additionally, a fiber optic component can be incorporated in the first and/or second balloons to allow the UV light to be generated from within the balloons, thus initiating the curing around the entire spacer, and not just at the point of injection.

Other cross linking chemistries include the use of amine containing polymers and/or monomers that could be reacted by the addition of aldehyde containing materials. The aldehyde/amine reaction is used to generally crosslink materials for various applications.

Different UV-curable or cross linkable materials can be used in the first and second balloons such that the mechanical properties for the first and second balloons are different. For example monomers could be chosen so that one of the balloons is stiffer than the other balloon after implantation.

In one embodiment, as shown in FIG. 2, the first and second filler materials 40, 60 are introduced separately into the first and second balloons, respectively, via first and second inlet ports 42, 62 that include, for example, self-sealing valves, such as one-way valves or other devices well known in the art. In an alternate embodiment, chambers provided by the first and second balloons are fluidly joined such that only one inlet port is necessary. In the single inlet port embodiment, the first and second balloons may be expanded simultaneously. Alternatively, in another single inlet port embodiment, a valve or membrane may connect a portion of the adjoining balloons interior to the spacer such that as the filler material is introduced into the first balloon, the first balloon expands until a certain interior pressure is achieved, at which point the valve or membrane interiorly connecting the first and second balloons yields to the pressure and enables the filler material to be introduced into the second balloon through the interior of the first balloon.

The UV curing process or the addition of an aldehyde or other cross linker chemistries can be used to seal the injection port of the spacer, regardless of whether the filler material is a UV curable or cross linkable material. This could be used in lieu of or in conjunction with a mechanical closure system, such as for example a valve, suturing or clamping the port closed. With the ability to seal the port with a UV curing or cross linking system, the filler material may take a longer period of time to solidify and/or transform into its final state without concern of the material excreting from the opening.

Furthermore, for radiographic visualization, the balloons may possess a radiopaque character so that the surgeon can visualize the positioning and orientation of the spacer as the spacer is being inserted, both before and after filling. For example, the spacer may include printing on the first and/or second balloons with a radiopaque ink. Alternatively, the first and/or second balloons may include a fiber, strand or band of radiopaque material inherent in the balloons that allow for visualization of the placement and orientation of the balloon(s). The filler materials may also incorporate radiopaque materials so that the entire spacer can be visualized radiographically after implantation. Alternatively, the filling tube can incorporate one or more radiopaque markings of known position relative to the first and/or second balloons to facilitate surgical placement and positioning via radiographic visualization.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An inflatable interspinous spacer for insertion into an interspinous space between adjacent superior and inferior spinous processes via a minimally invasive surgical procedure, the inflatable interspinous spacer including:

a first inflatable balloon having an insertable deflated condition and an inflated expanded condition, the first inflatable balloon including a first end portion having a first height, a second end portion having a second height and a central portion extending between the first and second end portions, the central portion having a third height, the first and second heights of the first and second end portions, respectively, being larger than the third height of the central portion when in the inflated expanded state so that the first inflatable balloon assumes an "H" or dumbbell-like shape, wherein the first, second, and central portions are expandably inflatable;

a first filler material configured for introduction into the first inflatable balloon to inflate the first inflatable balloon from the insertable deflated condition to the inflated expanded condition;

a second inflatable balloon characterized by a hollow form with a cylindrical outer surface, the second inflatable balloon having an insertable deflated condition and an inflated expanded condition, the second inflatable balloon being disposed around a circumference of the central portion of the first inflatable balloon and extends along a length of the central portion between the first and second end portions, wherein a height of the second inflatable balloon is less than a length of the second inflatable balloon as measured across a central longitudinal lumen of the second inflatable balloon; and a second filler material configured for introduction into the second inflatable balloon via a filling tube extending through a portion of the first inflatable balloon to an opening on an interior of the second inflatable balloon, the second filler material introduced to expand the second inflatable balloon from the insertable deflated condition to the inflated expanded condition;

wherein the first inflatable balloon is manufactured from a low compliant material so that upon inflation, the first balloon assumes a predetermined shape and the second inflatable balloon is manufactured from a semi-compliant or highly compliant material; and wherein the modulus of the first filler material is larger than the modulus of the second filler material.

2. An inflatable interspinous spacer for mounting between adjacent spinous processes during minimally invasive surgical procedures of the spine, the spacer including:
- a first inflatable member having an expanded and a non-expanded state, and including a central portion having a height, the central portion extending between first and second end portions, wherein the height of the first and second end portions is larger than the height of the central portion, wherein, in the expanded state, the first inflatable member assumes an "H" or dumbbell-like shape, wherein the first, second, and central portions are expandably inflatable;
- a first filler material configured for introduction into the first inflatable member to thereby cause the expansion of the first inflatable member;
- a second inflatable member characterized by a hollow form with a cylindrical outer surface, wherein the second inflatable member is only disposed around a circumference of the central portion of the first inflatable member between the first and second end portions, wherein a height of the second inflatable balloon is less than a length of the second inflatable balloon as measured across a central longitudinal lumen of the second inflatable balloon; and
- a second filler material configured for introduction into the second inflatable member via a filling tube extending through a portion of the first inflatable member to an opening on an interior of the second inflatable member, the second filler material introduced to thereby cause the expansion of the second inflatable member;
- wherein, upon expansion of the first and second inflatable members, the rigidity of the second inflatable member is less than the rigidity of the first inflatable member.

3. An inflatable spacer system for positioning between adjacent spinous processes comprising:
- a first balloon having a first end portion, a second end portion and a central portion located between the first and second end portions, the first end portion, the second end portion and the central portion being in fluid communication with each other, the first balloon having a flexible, low-compliant housing having an insertable condition and an inflated condition, the central portion and the first and second end portions in the inflated condition each having a height, wherein the first, second, and central portions are expandably inflatable;
- a first filler material configured for introduction into the first balloon to cause expansion of the first balloon;
- a second inflatable balloon having a flexible housing with a cylindrical outer surface disposed around a circumference of the central portion along a length of the central portion between the first end and the second end, wherein a height of the second inflatable balloon is less than a length of the second inflatable balloon as measured across a central longitudinal lumen of the second inflatable balloon, the second balloon having an insertable condition and an inflated condition; and
- a second filler material configured for introduction into the second inflatable balloon via a filling tube extending through a portion of the first inflatable balloon to an opening on an interior of the second inflatable balloon, the second filler material introduced to cause expansion of the second inflatable balloon,
- wherein in the insertable condition the spacer is laterally insertable into the interspinous space between adjacent spinal processes without substantially altering the spinal processes such that the central portion and at least a portion of the second balloon is located between the adjacent spinous processes and wherein in the inflated condition the first and second end portions are located along the lateral sides of the spinous processes and retain the spacer in position between the spinous processes, and,
- wherein in the inflated condition the second expandable balloon is less rigid than the first expandable balloon and the height of the end portions in the inflated condition is larger than the height of the central portion and the second balloon disposed over the central portion in the inflated condition.

4. The system of claim 3 wherein the housing of the second balloon is formed of a low-compliant material.

5. The system of claim 3 wherein the spacer in the expanded condition forms an "H" or dumbbell-like shape.

6. The system of claim 3 wherein the compressive modulus of the first filler material is less than the second filler material.

7. The system of claim 3 wherein the second balloon and the central portion in the expanded condition and when located between the spinous processes limits extension of the spine.

8. The system of claim 7 wherein the second balloon conforms to the shape of the spinous processes to increase the surface area contact between the spacer and the inferior and superior surfaces of the spinous processes.

9. The system of claim 3 wherein expansion of the second balloon distracts and expands the space between the adjacent spinous processes where the spacer is located.

10. The system of claim 3 wherein the second balloon is disposed around the circumference of the central portion and forms a common wall with at least a portion of the central portion.

11. The system of claim 3 wherein the housing of the second balloon is semicompliant.

12. The system of claim 3 wherein the second balloon is disposed over at least a portion of the first end portion and the second end portion.

13. The system of claim 3 wherein in the insertion condition the spacer comprising the first and second balloons without the first or second filler materials is insertable within a cannula having a 5 mm inside diameter.

14. The system of claim 3 wherein the second balloon absorbs compressive shocks to the spacer.

15. An inflatable spacer system for insertion between spinous processes comprising;
- a two balloon spacer having a first balloon and a second balloon, the two balloons forming a central zone, a first end zone and a second end zone, the two-balloon spacer having an insertable condition and an inflated condition wherein in the insertable condition the spacer is insertable within a cannula having a 5 mm inside diameter, and in the inflated condition a portion of each of the first end zone and second end zone is larger than the central zone, the central zone positionable between adjacent spinous processes to limit extension of the spine;
- wherein the second balloon surrounds a circumference of the central zone of the first balloon and extends along a length of the central zone between the first and second end zones, wherein the second balloon has a cylindrical outer surface, the second balloon configured in the inflated condition for contact with at least a portion of the spinous processes, the second balloon inflated via a filling tube that extends through a portion of the first balloon into an opening provided on an interior of the second inflatable balloon, the second balloon in the inflated condition being less rigid than the first balloon and configured to conform to the shape of the contacted spinous processes in order to increase the area of contact between the spinous processes and the second balloon, wherein a height of the second inflatable balloon is less than a length of the second inflatable balloon as measured across a central longitudinal lumen of the second inflatable balloon, wherein the first balloon, the second balloon, and the central zone are expandably inflatable.

* * * * *